United States Patent [19]
McAuley et al.

[11] Patent Number: 5,981,964
[45] Date of Patent: Nov. 9, 1999

[54] ADJUSTABLE X-RAY SHIELD AND ON-LINE DOSIMETRY SYSTEM USING SAME

[75] Inventors: Bruce J. McAuley, 15 Possum La., Portola Valley, Calif. 94028; Richard T. Geiger, Montara, Calif.

[73] Assignee: Bruce J. McAuley, Portola Valley, Calif.

[21] Appl. No.: 09/063,034

[22] Filed: Apr. 20, 1998

Related U.S. Application Data

[60] Provisional application No. 60/068,476, Dec. 22, 1997.

[51] Int. Cl.$^6$ ........................................................ G21F 3/00
[52] U.S. Cl. ....................................... 250/515.1; 250/519.1
[58] Field of Search .............................. 250/515.1, 519.1

[56] References Cited

U.S. PATENT DOCUMENTS

| | | |
|---|---|---|
| 3,967,129 | 6/1976 | Winkler . |
| 3,984,696 | 10/1976 | Collica et al. . |
| 4,062,518 | 12/1977 | Stivender et al. . |
| 4,254,341 | 3/1981 | Herr et al. . |
| 4,581,538 | 4/1986 | Lenhart . |
| 4,638,166 | 1/1987 | Baudro . |
| 4,852,141 | 7/1989 | Horn . |
| 5,006,718 | 4/1991 | Lenhart ................................ 250/515.1 |
| 5,015,864 | 5/1991 | Maleki . |
| 5,090,044 | 2/1992 | Kobayashi . |

OTHER PUBLICATIONS

Mavig—Mobile X–Ray–Shields brochure, Hänel GMBH.
Mavig—Medical Personel Radiation Protection Systems brochure, Hänel GMBH.
Mavig—Medical Personnel Radiation Protection Systems Assembly Model 6262 brochure, Hänel GMBH.
UST–400, UST–25 Physician's Radiation Shield brochure, United Shielding Corp.
Most Recent Disclosures Concerning The Minimization Of Radiation Exposure To The Examining Physician At Angiography Workplaces, Symposium On The Occasion Of The 75$^{th}$ German Congress Of Radiology 1994 in Wiesbaden, Feuerlein Verlag, Germany.

*Primary Examiner*—Kiet T. Nguyen
*Attorney, Agent, or Firm*—Young Law Firm, P.C.

[57] ABSTRACT

An adjustable X-ray shield for an X-ray procedure table includes a main support bar mounted substantially vertically on the table near a patient's waist level, the main support bar extending above and below a surface of the table; a first transversal support bar, the first transversal support bar being attached to the main support bar just below the table and extending substantially across a width of the table; a second transversal support bar, the second transversal support bar being pivotally mounted to the main support bar above the table and extending substantially across a width of the table; and a first longitudinal support bar, the first longitudinal support bar being pivotally mounted to the main support bar above the table and extending along a length of the table past the patient's chest level. At least one sheet of radio-opaque shielding material is attachable to each of the first transversal support bar, the second transversal support bar and the first longitudinal support bar. According to another embodiment, the adjustable radiation shield includes on-line radiation dosimetry, wherein at least one of the plurality of sheets of radio-opaque shielding material includes at least one radiation sensor. The radiation sensor or sensors are connectable to a data processing and display apparatus via a communication channel to allow the physician to view real time radiation readings from the display apparatus and to adjust the position of the plurality of sheets of radio-opaque shielding material in response to the readings to minimize exposure to radiation scatter.

31 Claims, 4 Drawing Sheets

FIG. 4

ADJUSTABLE X-RAY SHIELD AND ON-LINE DOSIMETRY SYSTEM USING SAME

This application claims benefit of Provisional No. 60/068,476 filed Dec. 12, 1997.

BACKGROUND OF THE INVENTION

1. Field of the Invention

The present invention pertains to the field of shielding structures for radiation procedure tables. In particular, the present invention pertains to adjustable X-ray shields for procedure tables and adjustable X-ray shielding systems using on-line radiation dosimetry.

2. Description of the Related Art

During certain procedures, for example, those involving the insertion of an intravascular catheter (procedures such as atherectomy, balloon angioplasty, stent placement and the like), patients are required to lay prone on an X-ray procedure table. The physician then inserts a guidewire or a catheter device through a small incision, often near the patient's groin, and advances the device through an artery to the target site.

To facilitate imaging of the intravascular device during use, the device may include a radio-opaque distal tip to allow the physician to guide the device under fluoroscopic observation to the desired site. During such procedures, the physician controls an X-ray tube, the source of the radiation used to visualize the target arterial site and the intravascular device, using a foot pedal. The X-ray tube is generally located underneath the table surface. The X-ray beam generated by the tube travels through the procedure table and the patient's body. The majority of the photons generated by the X-ray tube are scattered by the cells within the patient's body. A small portion of the generated X-ray beam, however, succeeds in traversing both the procedure table and the patient's body. A portion of the X-ray beam that traverses both the table and the patient's body reaches an image intensifier located above the patient. The image intensifier detects the photons, channels them through a photon multiplier and transfers the resulting intensified image to a display screen, which allows the physician to accurately guide the device.

Interventional procedures such as described above often take hours to complete, and may expose the physician and the patient to a significant amount of radiation that may, over time, pose serious health risks. To reduce the physician's exposure to scattered X-ray radiation, a number of protective measures have been implemented. The first of such protective measures is the use of X-ray shields. Several types of X-ray shields have been developed. Lenhart, for example, in U.S. Pat. No. 5,006,718, proposes a shield assembly wherein shielding material extends from the side of the table adjacent the physician to the floor. However, such shield, while affording an unobstructed view of the patient, does not appear to protect the physician from the large amount of radiation scattered from the patient's body and above the level of the table. Other solutions generally involve the use of horizontally disposed strips of radiation shielding material, such as disclosed by Collica et al. in U.S. Pat. No. 3,984,696, or the use of vertically disposed strips of radiation shielding material hung from a position above the patient's body, as disclosed in Lenhart, U.S. Pat. No. 4,581, 538 and Stivender et al., U.S. Pat. No. 4,062,518. However, both of these approaches appear to share common disadvantages. The first of these is that the physician's view of the patient, and the patient's view of the physician is severely impaired by the strips of shielding material. The second of these disadvantages appears to be an incomplete shielding of scattered radiation, in that significant portions of the patient's body are directly exposed to the physician. During the interventional X-ray procedure, a significant amount of scatter from these exposed portions may reach the physician, with deleterious health consequences. Moreover, with such conventional X-ray shields, unintended gaps in coverage may occur due to improperly positioned or repositioned shields, unknowingly exposing the physician to greatly increased radiation levels until the gap is discovered, if ever. Indeed, the shield often must be re-positioned during the procedure when the orientation of the X-ray tube is changed to change the imaging angle. Failure to properly reposition the shield thereafter may result in gaps in the shielding material. As X-ray radiation cannot be seen, heard or felt, such gaps may remain undiscovered and may expose the physician and other personnel in the procedure room to needlessly increased radiation levels.

The second of such protective measures to protect the physician from unwanted scatter is the so-called lead apron. The lead apron is an article of clothing donned by the physician prior to a catheter procedure. The lead apron generally covers at least the neck including the thyroid, the torso, and the thighs. Leaded eyeglasses may also be worn. The apron is effective in significantly reducing the physician's instantaneous and cumulative exposure to X-ray radiation over time, at least with respect to the areas covered by the apron. In contrast, uncovered areas, such as the physician's hands, arms and lower legs, are protected, if at all, solely by the table's X-ray shield. Common lead aprons are equivalent to a lead barrier of about 0.25 to 0.5 millimeters in thickness. However, such protection, while effective, does not come without discomfort to the physician. Indeed, such lead aprons commonly weigh about fifteen to twenty pounds. As the physician may be required to bend over the patient for periods of time often measured in hours, a significant proportion of the weight of the lead apron may be borne by the physician's lower back, shoulder and neck area. Supporting such weight can, over time, cause intense lower back, neck and shoulder pain, particularly for those suffering from already weakened backs.

What is needed, therefore, is an X-ray shield for an X-ray procedure table that more effectively protects the physician from X-ray scatter. What is also needed is an X-ray procedure shield for an X-ray procedure table that is highly effective in attenuating X-ray scatter while affording the physician a relatively unobstructed view of the patient during the X-ray procedure. What is also needed is an X-ray shield that is sufficiently effective in attenuating radiation to allow the physician to wear a lighter apron (e.g. one having a lower lead equivalency rating) or to allow the physician to safely forego wearing a lead apron or other uncomfortable protective gear altogether. Also needed are means for insuring, at all times, the proper positioning of the X-ray shield to achieve the greatest possible attenuation of radiation.

SUMMARY OF THE INVENTION

In accordance with the above-described objects and those that will be mentioned and will become apparent below, the adjustable X-ray shield for an X-ray procedure table, according to an embodiment of the present invention comprises:

a main support bar mounted substantially vertically on the table near a patient's waist level, the main support bar extending above and below a surface of the table;

a first transversal support bar, the first transversal support bar being attached to the main support bar just below the table and extending substantially across a width of the table;

a second transversal support bar, the second transversal support bar being pivotally mounted to the main support bar above the table and extending substantially across a width of the table; and a first longitudinal support bar, the first longitudinal support bar being pivotally mounted to the main support bar above the table and extending along a length of the table past the patient's chest level.

According to other exemplary embodiments, at least one sheet of radio-opaque shielding material is attachable to the first transversal support bar, the second transversal support bar and/or the first longitudinal support bar. The main support bar may include an outer support tube portion below the table; an upper support tube portion above the table; and a telescoping support bar slidingly mounted at least within the upper support tube, the telescoping support bar allowing adjustment of a height of the second transversal and first longitudinal support bars above the surface of the table. The first transversal support bar may include a telescoping extender bar to accommodate X-ray procedure tables of varying widths. The first longitudinal support bar may comprise an articulated joint.

The adjustable X-ray shield may further comprise a first sheet of shielding material attached to the first transversal support bar that substantially spans the width of the table from an underside thereof to a floor surface. A second sheet of radio-opaque shielding material may be attached to the second transversal support bar adjacent the main support bar, the second sheet shielding material draping alongside the patient's pelvic and thigh areas to attenuate X-ray scatter therefrom. A third sheet of radio-opaque shielding material may be attached at least to the second transversal support bar, the third sheet of shielding material being of a generally rectangular shape and having a cutout portion for the patient's waist. The sheets of radio-opaque shielding material may provide overlapping coverage along the vertical axis of the main support bar. The main, first transversal, second transversal and first longitudinal support bars may be formed of metal and/or a radiolucent material. The radiolucent material may be a carbon fiber material.

According to other embodiments, the X-ray shield may be removably secured to the table by means of a clamping assembly. The clamping assembly may comprise at least two mounting pads to be positioned on the table surface and a bell crank mechanism attached underneath the table surface to the first transversal support bar. A first end of the first transversal support bar may be attached to the main support bar and a second end thereof may be attached to an outer support tube. The bell crank mechanism may comprise:

a pair of center pivots, each attached near respective ends of the first transversal support bar; a pair of rectangular blocks, each pivotally attached to respective ends of each of the center pivots closest to an underside of the table; and a pair of threaded cylinders, each attached to respective other ends of each of the center pivots and disposed within respective threaded through bores in each of the main support bar and outer support tube. Tightening the pair of threaded cylinders within the threaded through bores causes the pair of rectangular blocks to exert a force on the table to secure the X-ray shield thereto.

According to still further embodiments, the second transversal and first longitudinal support bars may be pivotally attached to the main support bar by respective clevis joints having respective pivot pins. In that case, tightening the respective pivot pins increases the friction in the respective clevis joints. A first end of the first transversal support bar may be attached to the main support bar and a second end thereof may be attached to an outer support tube and the X-ray shield may further comprise a second longitudinal support bar attached to the outer support tube such that the second longitudinal support bar is parallel to the first longitudinal support bar and disposed on an opposite side of the table; and a further sheet of radio-opaque shielding material attached to the second longitudinal support bar, to attenuate X-ray scatter on the opposite side of the table.

According to another embodiment, at least one of the sheets of radio-opaque shielding material may comprise one or more radiation sensors. One or more of the sensors may be a semiconductor X-ray sensor, such as a Cadmium-Zinc-Telluride (CdZnTe) sensor in communication with a data processing and display device. A plurality of X-ray sensors may be attached to each of the one or more sheets of radio-opaque shielding material, to form an array of X-ray sensors, the array of sensors being connected to a data processing and display device to allow real time monitoring of X-ray radiation from the X-ray shield. One or more of the sensors may be attachable to the patient's back or to the table, to measure the patient's entrance dose of radiation. Moreover, one or more of the sensors may be attachable to a person other than the patient, such as the physician and/or other care givers, to measure scatter received by that person during a procedure on the patient.

According to another embodiment, the present invention is a kit for an adjustable X-ray shield for a procedure table, comprising:

a main support bar, mountable substantially vertically on the table near a patient's waist level, such that the main support bar extends above and below a surface of the table;

a first transversal support bar, attachable to the main support bar just below the table to extend substantially across a width of the table;

a second transversal support bar, pivotally mountable to the main support bar above the table to extend across a width of the table;

a first longitudinal support bar, pivotally mountable to the main support bar above the table to extend along a length of the table past the patient's chest level; and at least one sheet of radio-opaque shielding material attachable to at least one of the first transversal support bar, the second transversal support bar and the first longitudinal support bar.

According to another embodiment of the kit according to the present invention, the sheet or sheets of radio-opaque shielding material may comprise at least one X-ray sensor attached thereto.

According to a further embodiment, the present invention is an X-ray shield for a procedure table, comprising:

a first sheet of radio-opaque shielding material adjustably disposed alongside the procedure table, from a distance above a surface of the table to a floor surface;

a second sheet of radio-opaque shielding material adjustably disposed across and above the surface of the table at a level of a patient's waist; and a third sheet of radio-opaque shielding material disposed across a width of the table from just underneath the table to about the floor surface, the first, second and third sheets of radio-opaque shielding material being supported by an adjustable frame assembly attached to the table.

According to a still further embodiment, a procedure table radiation shield having on-line radiation dosimetry according to the present invention comprises a plurality of sheets of radio-opaque shielding material adjustably disposed on a frame assembly so as to protect a physician from radiation scatter during a radiation procedure, at least one of the plurality of sheets of radio-opaque shielding material including at least one radiation sensor.

According to further embodiments, the array of radiation sensors may include at least one X-ray sensor, which may be a semiconductor X-ray sensor. Such a semiconductor X-ray sensor may be a CdZnTe sensor. The radiation sensor or sensors may be connectable to a data processing and display apparatus via a communication channel to allow the physician to view real time radiation readings from the display apparatus and to adjust a position of the plurality of sheets of radio-opaque shielding material in response to the readings to minimize exposure to radiation scatter during a radiation procedure. One or more of the radiation sensors may be attached to one of the sheets of radio-opaque shielding material and one or more of the radiation sensors may be adapted to be positioned anywhere within the procedure room or on a person within the procedure room.

BRIEF DESCRIPTION OF THE DRAWINGS

For a further understanding of the objects and advantages of the present invention, reference should be made to the following detailed description, taken in conjunction with the accompanying figures.

DESCRIPTION OF THE PREFERRED EMBODIMENTS

Figure 1:
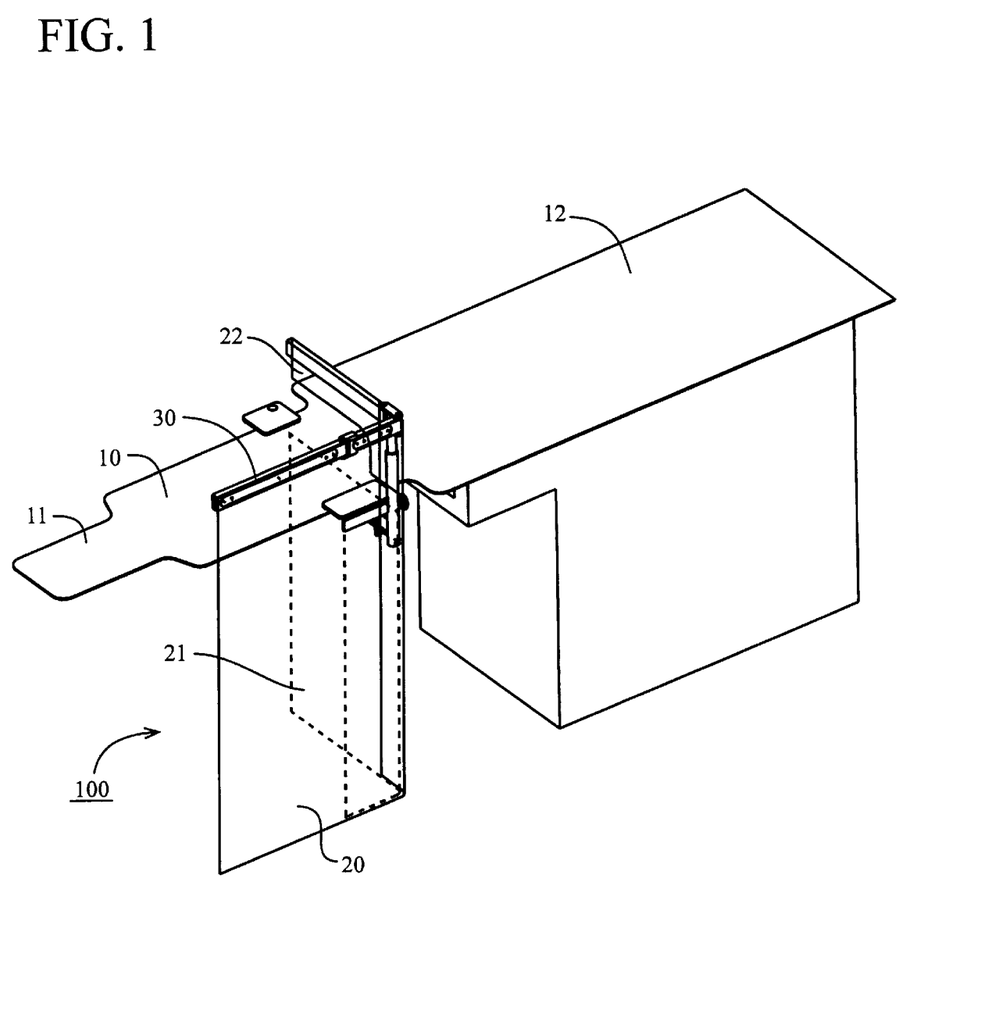
FIG. 1 shows a perspective view of an X-ray procedure table and an embodiment of the adjustable X-ray shield according to the present invention attached thereto.

FIG. 1 is a perspective view of a typical X-ray procedure table 10 and an embodiment of the adjustable X-ray shield 100 according to the present invention attached thereto. During a catheter procedure, for example, the patient's head rests on the narrow portion 11 of the table 10, while the patient's feet lie toward the wide portion 12 of the table 10. The physician normally stands to the patient's right, near waist level. The shape of the table 10, it is to be understood, may vary from that shown in FIG. 1.

Figure 3:
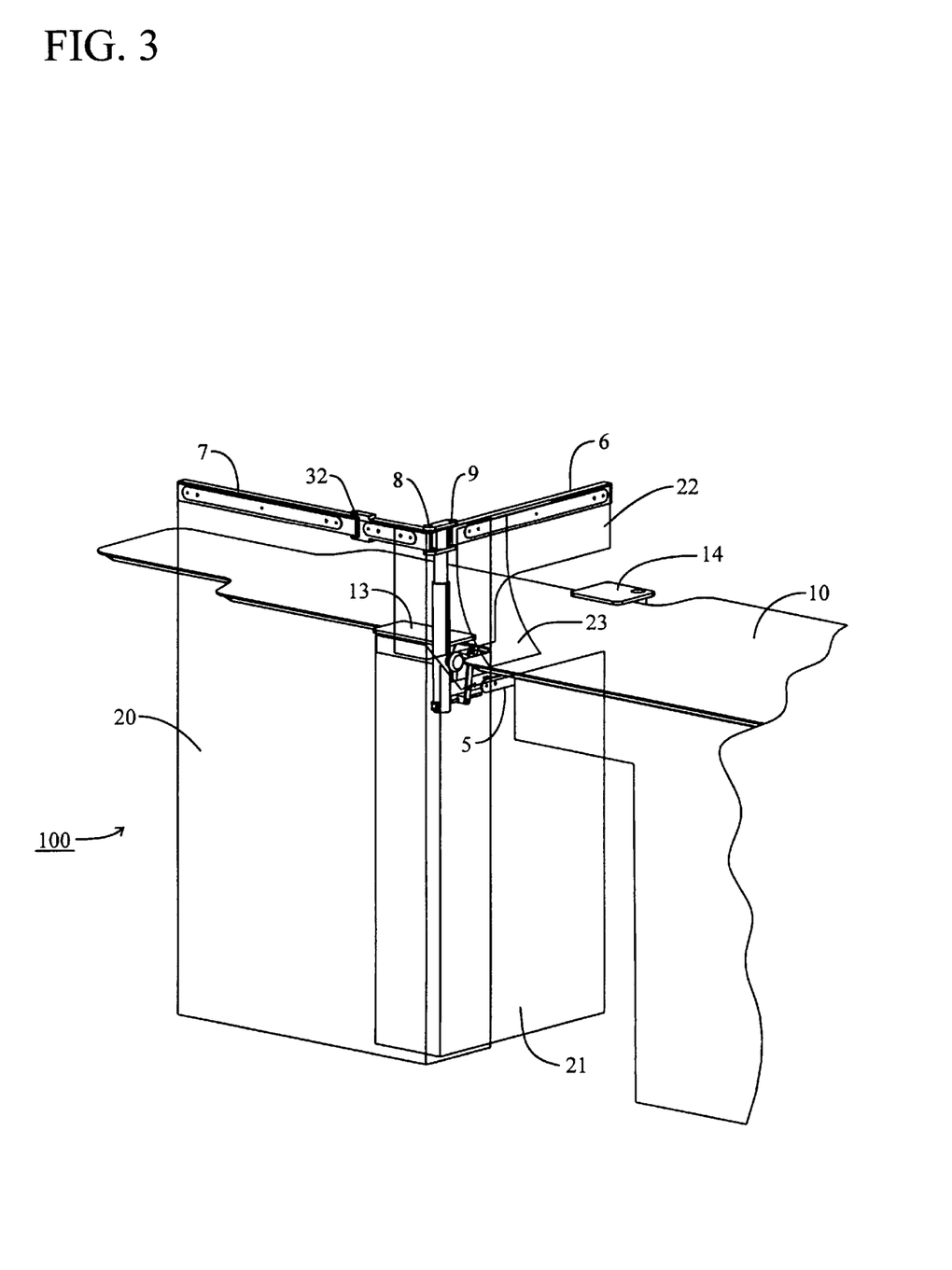
FIG. 3 is another perspective view of an embodiment of the adjustable X-ray shield according to the present invention, illustrating the manner in which the sheets of radio-opaque material may be attached to the adjustable frame assembly.

The embodiment of the adjustable X-ray shield 100 shown in FIG. 1 includes an adjustable frame assembly 30 attached to the table 10, and a plurality of sheets of radio-opaque shielding material attached thereto, such as sheets 20, 21, 22 and 23 (best shown in FIG. 3). The sheets of radio-opaque material 20, 21, 22 and 23 may include lead or any material suitable for blocking or attenuating radiation of other wavelengths. The sheet of radio-opaque shielding material 20, according to an embodiment of the present invention, is adjustably disposed alongside the procedure table 10, from an adjustable distance above the surface of the table 10 to about the surface of the floor. The sheet of radio-opaque shielding material 22 is adjustably disposed across and above the surface of the table 10, at about the patient's waist level, as the patient (not shown) lays on the table 10. The sheet 22 may have a generally rectangular shape and may include a cutout portion to accommodate the patient's waist or legs. The sheet of radio-opaque shielding material 21 is disposed across the width of the table 10, generally at the level of the patient's waist on the table 10, and spans the distance from just underneath the table 10 to about the surface of the floor.

According to the present invention, the sheets of radio-opaque shielding material 20, 21 and 22 at least partially surround the X-ray tube (not shown), which is generally located within the corner formed by the shields 20 and 21. Investigations into the sources of radiation during interventional procedures have revealed that some direct radiation may reach the physician as a result of a less than perfectly collimated X-ray source, and that substantial amounts of radiation are scattered by the table and the patient's body. A substantial portion of this scatter, it has been found, is directed back underneath the table, toward the physician's lower body. The sheet 21, according to the present invention, protects the physician from this X-ray scatter directed back underneath the table by substantially partitioning the X-ray tube from the physician. Another portion of radiation travels through the patient's body, and is scattered thereby, in all directions. It has further been found that, of this scatter, a substantial portion emerges through the patient's hip and thigh region, near the physician. This unexpected finding is addressed in the present invention by providing at least one sheet of radio-opaque material 22 across the patient's hips and waist, at an adjustable distance above the surface of the procedure table 10. The sheet 22, disposed across the width of the table 10, protects the physician from the scatter that originates from the patient's body. In this manner, the physician is further protected against harmful scatter, particularly scatter originating from the table itself and from the patient's body.

Figure 2:
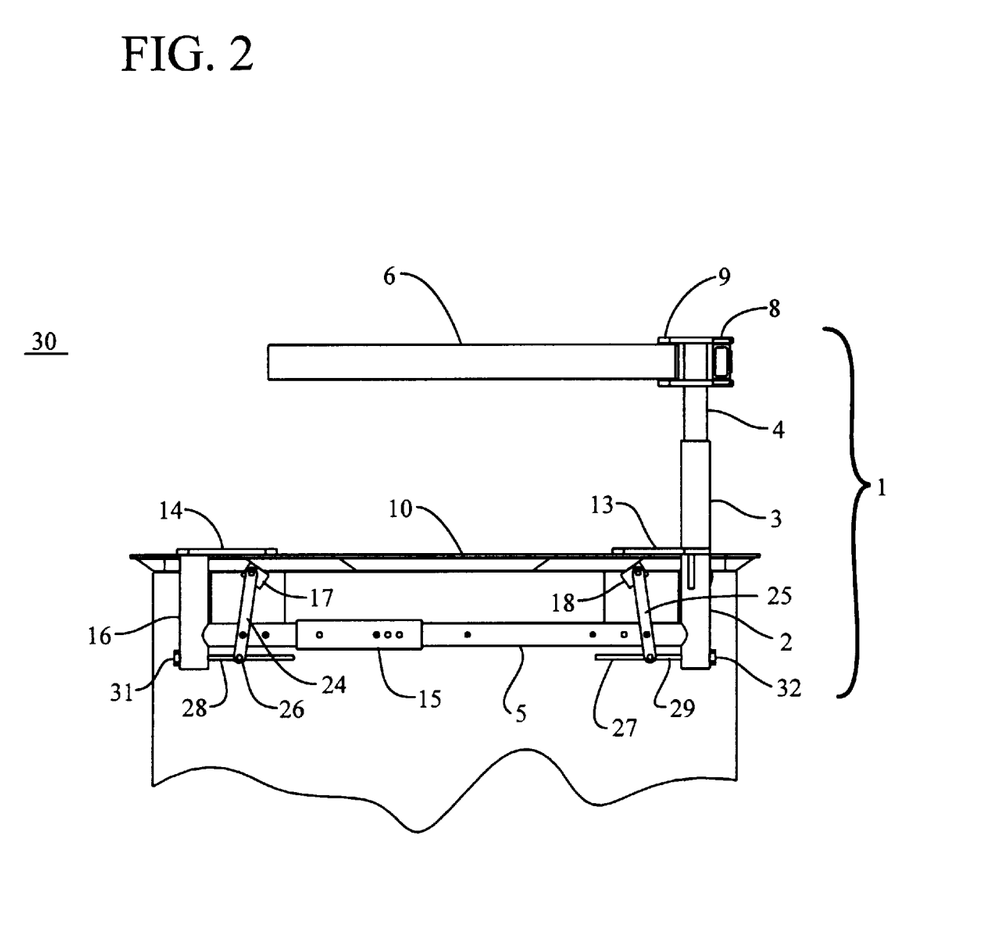
FIG. 2 shows a side view of the adjustable frame assembly of the adjustable X-ray shield according to the present invention, illustrating details of an embodiment of the clamping assembly thereof.

FIG. 2 shows a side view of the adjustable frame assembly 30 of an embodiment of the adjustable X-ray shield according to the present invention, whereas FIG. 3 shows a perspective elevation view of the adjustable X-ray shield 100. Considering now FIGS. 2 and 3 collectively, the frame assembly 30 of the adjustable X-ray shield 100 includes a main support bar 1 mounted substantially vertically on the table 10 near the patient's waist level. The main support bar 1 extends both above the surface of the table 10 and underneath the table 10. A first transversal support bar 5 is attached to the main support bar 1 just below the table 10. The first transversal support bar 5 extends across the width of the table 10 or across a substantial portion thereof, as best shown in FIG. 3. A second transversal support bar 6 is pivotally mounted to the main support bar 1 above the surface of the table 10 and also extends across the width of the table 10 or a substantial portion thereof, as shown in FIGS. 2 and 3. A first longitudinal bar 7, shown in FIG. 3, is pivotally mounted to the main support bar 1 above the surface of the table 10 and extends along a portion of the length of the table 10 from the main support bar 1 to at least past the patient's chest. As shown in FIG. 3, the first longitudinal support bar 7 may include an articulated joint 32, thereby allowing the physician to swing a portion of the first longitudinal support bar 7 and any attached sheet of radio-opaque shielding material away from the table 10. The first transversal, the second transversal and the first longitudinal support bars 5, 6 and 7 may be made from metal such as stainless steel or aluminum, from a radiolucent material, such as carbon fiber or from a combination thereof.

As shown in FIGS. 2 and 3, the second transversal and the first longitudinal bars 6, 7 are pivotally attached to the main support bar 1 by respective clevis joints 9, 8 having respective pivot pins (not shown). Tightening the pivot pins increases the friction in the levis joints 9, 8.

The main support bar 1 includes an outer support tube 2 below the table 10, an upper support tube 3 above the table 10 and a telescoping support bar 4 slidingly mounted at least within the upper support tube 3. The telescoping support bar 4 allows the height of the second transversal and first longitudinal support bars 6, 7 and thus of the sheets 20, 22 and 23 to be adjusted above the surface of the table to accommodate the patient's body habitus and to provide optimal radiation attenuation.

For applications in which shielding is desired for personnel positioned on the side of the table 10 opposite to the side closest to the first longitudinal support bar 7 (the patient's left side as he or she is laying on the procedure table 10), a second upper support assembly, similar to upper support assembly 3, may be attached to the outer support tube 16. A second longitudinal support bar may then be attached by a clevis joint to the second upper support assembly. When a sheet of radio-opaque shielding material similar to sheet 20 is attached to this second longitudinal support bar, additional shielding on the patient's left side will be obtained. The second upper support assembly, the second longitudinal support bar, the levis joint connecting the two, as well as the sheet of radio-opaque shielding material attached to the second longitudinal support bar are not shown, for clarity, as their structures are similar to their counterparts on the patient's right side.

For applications in which it is anticipated that X-ray scatter will be a factor above the level of the second transversal and first longitudinal support bars 6, 7, additional shielding may be required. This may be achieved by means of a ceiling mounted transparent leaded acrylic shield with a 1 millimeter lead equivalency, which is available from, for example, Minex Engineering, Antioch, Calif.

As shown in FIG. 2, the first transversal support bar 5 includes a telescoping extender bar 15, allowing the adjustable frame assembly 30 according to the present invention to accommodate procedure tables of varying widths. The X-ray shield according to the present invention may be integral to the procedure table 10. Alternatively, as shown in both FIGS. 2 and 3, the X-ray shield according to the present invention may be removably attached to the table 10 by means of a clamping assembly. Preferably, as in the embodiment shown in FIG. 2, the upper support tube 3 should be removable, allowing the clamping assembly to remain attached to the table 10 at all times, if the adjustable shield according to the present invention is not to be used for a particular case.

The clamping assembly may include mounting pads 13 and 14, which mounting pads support the adjustable frame assembly 30 on the table 10. The mounting pads 13 and 14 are placed on opposite sides and across the width of the procedure table 10. The separation between the mounting pads 13 and 14 is adjustable by means of the telescoping extender bar 15 of the first transversal support bar 5. According to one embodiment of the present invention, the clamping assembly includes a bell crank mechanism attached to the first transversal support bar 5 underneath the table 10 to secure the adjustable frame assembly 30 to the table 10. As shown in FIG. 2, the bell crank mechanism may include a pair of rectangular blocks 17, 18 each of which is pivotally attached to one end of a pair of center pivots 24, 25, respectively. The pair of rectangular blocks 17, 18 may be made of hard plastic or from other suitably hard material. The pair of rectangular blocks 17, 18 may be attached to the pair of center pivots 24, 25 by a pair of screws, for example. Likewise, the pair of center pivots 24, 25 may also be pivotally attached to the first transversal support bar 5 by means of screws or other suitable fasteners. Attached to the other end of the center pivots 24, 25 are a pair of threaded cylinders 26, 27, respectively. The threaded cylinders 26, 27 include respective cylinder threads 28, 29. The threaded cylinders 26, 27 are inserted through a threaded bore within the outer support tube 16 and the outer support tube 2 of the main support tube 1. Turning the threaded cylinder heads 31, 32 of the threaded cylinders 26, 27, respectively, causes the rectangular blocks 17, 18 to act like cams on the undersurface of the table 10 and exert a force thereon. The table 10 is then squeezed between the two rectangular blocks 17, 18, catching respective edges of the underside of the table 10. The rectangular blocks 17, 18 also exert a force component toward the mounting pads 14 and 13, respectively, further securing the adjustable frame assembly 30 to the table 10.

It is to be noted that the embodiment of the clamping assembly described herein and shown in the referenced figures is but one of many possible embodiments of such a clamping assembly. Indeed, any such clamping assembly that is effective in securing the adjustable frame assembly 30 to the table 10 may be implemented within the context of the present invention. Whichever clamping assembly is implemented, however, must attach the adjustable frame assembly 30 to the table 10 with sufficient strength to allow the frame assembly to securely and safely support the combined weight of at least the sheets of radio-opaque shielding material 20, 21, 22 and 23.

As shown in FIG. 3, at least one sheet of radio-opaque shielding material, such as sheets 20, 21, 22 and 23, is attachable to the first transversal support bar 5, the second transversal support bar 6 and the first longitudinal support bar 7. For example, the second transversal support bar 6 may support not only the sheet 22 having the cutout portion therein, but also another sheet of radio-opaque shielding material 23 draped over the patient's pelvic and thigh areas to attenuate scatter therefrom. The sheet 23 may be a rectangular sheet of radio-opaque material and may be attached to the second transversal support 6 adjacently to the main support bar 1. Providing additional shielding, the sheet of radio-opaque material 21 is particularly effective in attenuating X-ray scatter originating from underneath the table, while affording the physician with unobstructed space in which to stand. Such sheet 21 is attached to the first transversal support bar 5 and spans substantially the width of the table 10 from just underneath the table 10 to the floor surface. As shown in FIG. 2, the sheets of radio-opaque shielding material may overlap one another, to provide overlapping coverage along at least the vertical axis of the main support bar 1. Moreover, overlapping coverage may also be indicated on the patient's left side, along the axis of the second upper assembly support bar attached to the outer support tube 16, if the patient's left side is to be shielded. This overlapping coverage provides additional shielding when, for example, the second transversal and the first longitudinal support bars 6, 7 are swung away from their depicted positions. Such repositioning of the radio-opaque sheets may be necessary when the imaging angle is changed during a procedure. Preferably, the sheets 20, 21, 22 and 23 have at least a 1 millimeter lead equivalency rating. The sheets 20, 21, 22 and 23 may be attached to their respective support bars 7, 5, and 6 by any suitable means. Preferably, such attachment means allow the sheets 20, 21, 22 and 23 to be removable from the adjustable frame assembly 30. For example, VELCRO® hook and loop fasteners may be utilized with good results.

The adjustable X-ray shield according to the present invention, as described and illustrated herein, is believed to be highly effective in blocking a substantial portion of scatter from the procedure table 10 itself, as well as from the patient's body. Accordingly, the present invention may allow the physician to dispense with a high lead equivalency (heavy) lead apron, or to dispense with the lead apron altogether. However, to insure the safety of the physician and that of other personnel present in the operating room, it is prudent to monitor the effectiveness of the adjustable shield. Moreover, as the shield must often be reconfigured and moved to accommodate changes in position of the X-ray tube, such monitoring should preferably be substantially constant to insure that the shield is optimally configured at all times to protect the physician from X-ray or other radiation scatter.

Figure 4:
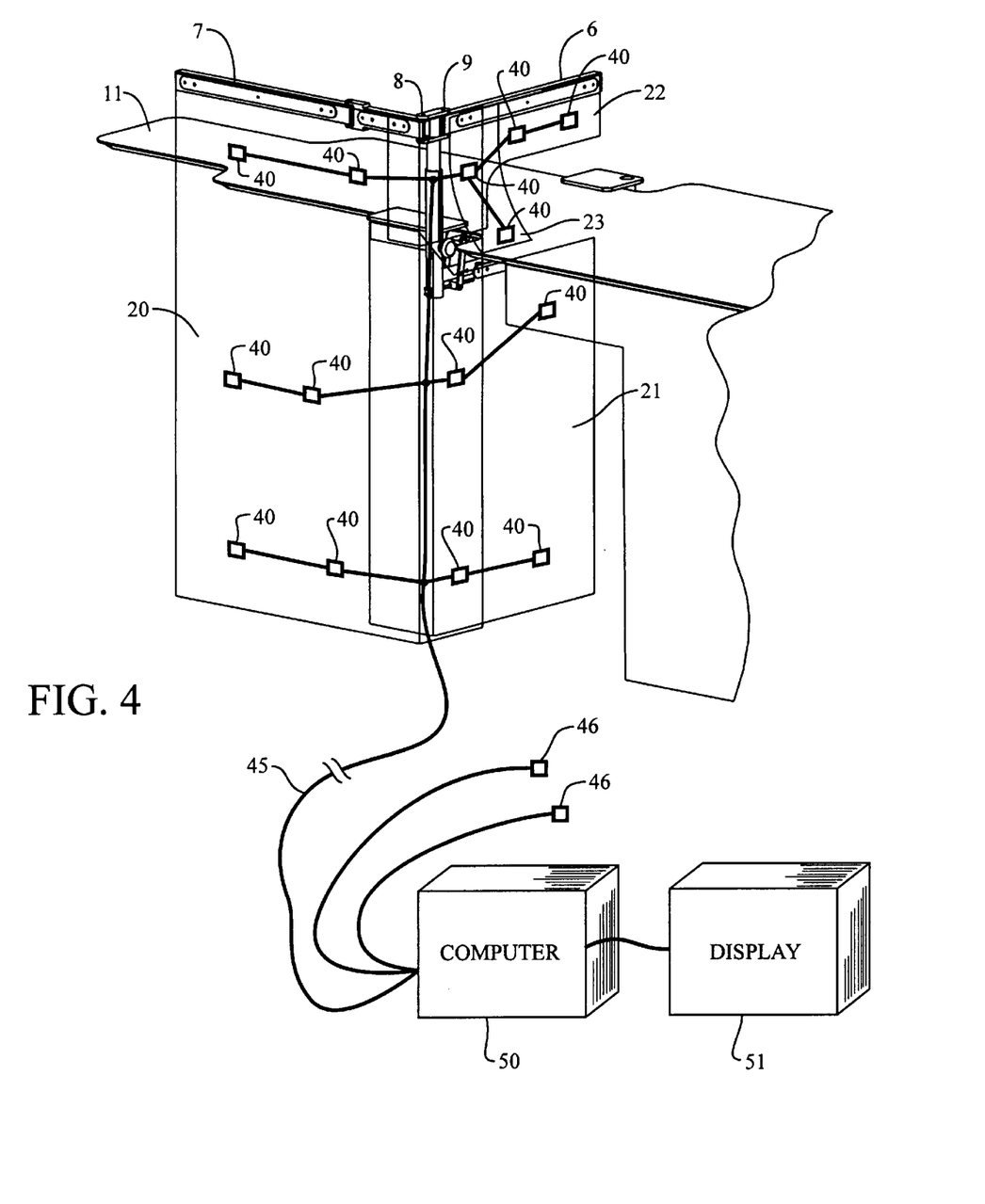
FIG. 4 illustrates another embodiment of the present invention, including an array of radiation sensors for real-time monitoring of radiation scatter.

According to another embodiment of the adjustable shield according to the present invention, at least one of the sheets of radio-opaque shielding material 20, 21, 22 and 23 (as well as those on the patient's left side, if present) includes at least one radiation sensor, such as an X-ray sensor. FIG. 4 shows an embodiment of an adjustable radiation shield according to the present invention, wherein the sheets 20, 21, 22 and 23 include a plurality of X-ray sensors attached thereto. The plurality of X-ray sensors 40 of FIG. 4 form an array of sensors that are connected to a data processing and display device, such as a computer 50 and a display 51. The display 51 is preferably visible to the physician during the interventional procedure, to allow the physician to monitor, in real time, the efficacy and proper deployment of the adjustable shield according to the present invention. The array of sensors 40 may be connected to the data processing and display device via a communication link 45, which may include wires, or may be a wireless communication channel. A plurality of additional sensors 46 (only two of which are shown in FIG. 4) are provided, which may be strategically placed anywhere in the operating room, or may be worn on the physician's or other caregiver's person, to provide a direct reading of the amount of radiation the physician (or other personnel in the room) is receiving and/or has cumulatively received. One of these additional sensors 46 may also be attached to the patient's back or to the table, to measure the patient's entrance dose of X-ray radiation. Although the additional sensors 46 are shown, in FIG. 4, as being attached to the computer 50, they may alternatively be connected to and form an integral part of the array of sensors 40 instead.

The sensors 40, 46 may be semiconductor X-ray sensors, such as CdZnTe radiation sensors, available from eV Products, Saxonburg, Pa. The sensors 40 may be attached to the sheets 20, 21, 22 and 23 or may be sewn therein.

The data processing and display device preferably allows the physician to view, in real time, his or her instantaneous radiation dose, as well as his or her cumulative radiation dose. Entrance dose data from the sensor attached to the patient's back may also be displayed. Historical radiation data for the physician may be stored within the data processing device 50, and such data may be later accessed and thereafter updated by entering a physician ID code, for example. In this manner, an accurate and timely source of radiation dose data may be acquired and maintained for each physician using the adjustable X-ray shield according to the present invention. According to one embodiment, the display 51 may display a graphical representation of the shield and radiation level indicia adjacent thereto or superimposed thereon. Such indicia may include color, numerical data or other perceptible and intuitive indication of radiation levels. To acquire the relevant radiation data, the sensors 40, 46 may be periodically polled, may generate interrupt signals, or may utilize some other protocol, thereby allowing the data processing and display unit to process and display real time radiation scatter data. Utilizing this real time information, the physician may make timely adjustments to the adjustable shield of the present invention to insure that it is optimally positioned at all times during a procedure. In this manner, the physician forms part of a feedback loop, alternately adjusting the shield and observing the resultant changes in the readings of the sensors 40, 46 on the display 51. Appropriate data acquisition and rendering software should be loaded and running on the computer 50. Should the display unit 51 show that one or more of the semiconductor sensors 40, 46 are registering an unacceptable level of scatter, an alarm may sound and the physician may then make any appropriate adjustments to the shield during the procedure to minimize radiation exposure.

While the foregoing detailed description has described several embodiments of this invention, it is to be understood that the above description is illustrative only and not limiting of the disclosed invention. For example, the clamping assembly described herein may be varied to suit the particular procedure table utilized. Other details of the frame assembly or sheets of radio-opaque material may vary from that described and illustrated herein, without, however, departing from the spirit and scope of the present invention. For example, a letter "J" shaped rigid support member may be slid under the patient's right thigh and a sheet of radio-opaque shielding material may be draped thereon, to further protect the physician from scatter directed orthogonally from the patient's thigh. A number of other modifications will no doubt occur to persons of skill in this art. All such modifications, however, should be deemed to fall within the scope of the present invention. Thus, the invention is to be limited only by the claims as set forth below.

What is claimed is:

1. An adjustable X-ray shield for an X-ray procedure table, comprising:

a main support bar mounted substantially vertically on the table near a patient's waist level, the main support bar extending above and below a surface of the table;

a first transversal support bar, the first transversal support bar being attached to the main support bar just below the table and extending substantially across a width of the table;

a second transversal support bar, the second transversal support bar being pivotally mounted to the main support bar above the table and extending substantially across the width of the table; and a first longitudinal support bar, the first longitudinal support bar being pivotally mounted to the main support bar above the table and extending along a length of the table past the patient's chest level.

2. The adjustable X-ray shield of claim 1, further comprising at least one sheet of radio-opaque shielding material attachable to each of the first transversal support bar, the second transversal support bar and the first longitudinal support bar.

3. The adjustable X-ray shield of claim 2, wherein at least one of the sheets of radio-opaque shielding material comprises at least one sensor.

4. The adjustable X-ray shield of claim 3, wherein said at least one sensor is a semiconductor X-ray sensor connected to a data processing and display device.

5. The adjustable X-ray shield of claim 4, wherein said at least one X-ray sensor is a CdZnTe radiation sensor.

6. The adjustable X-ray shield of claim 3, wherein a plurality of X-ray sensors are attached to each of the at least one of the sheets of radio-opaque shielding material to form an array of X-ray sensors, the array of sensors being in communication with a data processing and display device to allow real time monitoring of X-ray radiation from the X-ray shield.

7. The adjustable X-ray shield of claim 3, wherein at least one of the sensors is attachable to one of a back of a patient and the table, to measure the patient's entrance dose of radiation.

8. The adjustable X-ray shield of claim 3, wherein at least one of the sensors is attachable to a person other than the patient, to measure scatter received by the person during a procedure on the patient.

9. The adjustable X-ray shield of claim 1, wherein the main support bar includes:
    an outer support tube portion below the table;
    an upper support tube portion above the table; and
    a telescoping support bar slidingly mounted at least within the upper support tube, the telescoping support bar allowing adjustment of a height of the second transversal and first longitudinal support bars above the surface of the table.

10. The adjustable X-ray shield of claim 1, wherein the first transversal support bar includes a telescoping extender bar to accommodate X-ray procedure tables of varying widths.

11. The adjustable X-ray shield of claim 1, wherein the first longitudinal support bar comprises an articulated joint.

12. The adjustable X-ray shield of claim 1, further comprising a first sheet of shielding material attached to the first transversal support bar that substantially spans the width of the table from an underside thereof to a floor surface.

13. The adjustable X-ray shield of claim 1, further comprising a second sheet of radio-opaque shielding material attached to the second transversal support bar adjacent the main support bar, the second sheet of shielding material draping alongside the patient's pelvic and thigh areas to attenuate X-ray scatter therefrom.

14. The adjustable X-ray shield of claim 1, further comprising a third sheet of radio-opaque shielding material attached at least to the second transversal support bar, the third sheet of shielding material being of a generally rectangular shape and having a cutout portion for the patient's waist.

15. The adjustable X-ray shield of claim 1, further comprising sheets of radio-opaque shielding material, the sheets of radio-opaque shielding material providing overlapping coverage along a vertical axis of the main support bar.

16. The adjustable shield of claim 1, wherein the main, first transversal, second transversal and first longitudinal support bars are formed of at least one of metal and a radiolucent material.

17. The adjustable shield of claim 16, wherein the radiolucent material is a carbon fiber material.

18. The adjustable X-ray shield of claim 1, wherein the X-ray shield is removably secured to the table by means of a clamping assembly.

19. The adjustable X-ray shield of claim 18, wherein the clamping assembly comprises at least two mounting pads to be positioned on the table surface and a bell crank mechanism attached underneath the table surface to the first transversal support bar.

20. The adjustable X-ray shield of claim 19, wherein a first end of the first transversal support bar is attached to the main support bar and a second end thereof is attached to an outer support tube, and wherein the bell crank mechanism comprises:
    a pair of center pivots, each attached near respective ends of the first transversal support bar;
    a pair of rectangular blocks, each pivotally attached to respective ends of each of the center pivots closest to an underside of the table; and
    a pair of threaded cylinders, each attached to respective other ends of each of the center pivots and disposed within respective threaded through bores in each of the main support bar and outer support tube;
    whereby, tightening the pair of threaded cylinders within the threaded through bores causes the pair of rectangular blocks to exert a force on the table to secure the X-ray shield thereto.

21. The adjustable X-ray shield of claim 1, wherein the second transversal and first longitudinal support bars are pivotally attached to the main support bar by respective clevis joints having respective pivot pins, and wherein tightening the respective pivot pins increases a friction in the respective clevis joints.

22. The adjustable X-ray shield of claim 1, wherein a first end of the first transversal support bar is attached to the main support bar and a second end thereof is attached to an outer support tube and wherein the X-ray shield further comprises:
    a second longitudinal support bar attached to the outer support tube such that the second longitudinal support bar is parallel to the first longitudinal support bar and disposed on an opposite side of the table; and
    a further sheet of radio-opaque shielding material attached to the second longitudinal support bar, to attenuate X-ray scatter on the opposite side of the table.

23. A kit for an adjustable X-ray shield for a procedure table, comprising:
    a main support bar, mountable substantially vertically on the table near a patient's waist level, such that the main support bar extends above and below a surface of the table;
    a first transversal support bar, attachable to the main support bar just below the table to extend substantially across a width of the table;
    a second transversal support bar, pivotally mountable to the main support bar above the table to extend across a width of the table;
    a first longitudinal support bar, pivotally mountable to the main support bar above the table to extend along a length of the table past the patient's chest level; and
    at least one sheet of radio-opaque shielding material attachable to at least one of the first transversal support bar, the second transversal support bar and the first longitudinal support bar.

24. The kit of claim 23, wherein the at least one sheet of radio-opaque shielding material comprises at least one X-ray sensor attached thereto.

25. An X-ray shield for a procedure table, comprising:
a first sheet of radio-opaque shielding material adjustably disposed alongside the procedure table, from a distance above a surface of the table to a floor surface;
a second sheet of radio-opaque shielding material adjustably disposed across and above the surface of the table at a level of a patient's waist; and
a third sheet of radio-opaque shielding material disposed across a width of the table from just underneath the table to about the floor surface, the first, second and third sheets of radio-opaque shielding material being supported by an adjustable frame assembly attached to the table.

26. A procedure table radiation shield having on-line radiation dosimetry, comprising a plurality of sheets of radio-opaque shielding material adjustably disposed on a frame assembly so as to protect a physician from radiation scatter during a radiation procedure, at least one of the plurality of sheets of radio-opaque shielding material including at least one radiation sensor.

27. The shield of claim 26, wherein the at least one radiation sensor includes at least one X-ray sensor.

28. The shield of claim 27, wherein the at least one X-ray sensor is a semiconductor X-ray sensor.

29. The shield of claim 27, wherein the at least one X-ray sensor is a CdZnTe sensor.

30. The shield of claim 26, wherein the at least one radiation sensor is connectable to a data processing and display apparatus via a communication channel to allow the physician to view real time radiation readings from the display apparatus and to adjust a position of the plurality of sheets of radio-opaque shielding material in response to the readings to minimize exposure to radiation scatter during a radiation procedure.

31. The shield of claim 26, wherein at least one of the radiation sensors is attached to one of the sheets of radio-opaque shielding material and wherein at least one of the radiation sensors is adapted to be positioned anywhere within a procedure room or on a person within the procedure room.

* * * * *